United States Patent
Sassa et al.

(10) Patent No.: US 12,151,010 B2
(45) Date of Patent: Nov. 26, 2024

(54) SKIN LIGHTENING AGENT

(71) Applicant: POLA CHEMICAL INDUSTRIES, INC., Shizuoka (JP)

(72) Inventors: Shoko Sassa, Kanagawa (JP); Yasuhito Mori, Kanagawa (JP); Yuko Saitoh, Kanagawa (JP)

(73) Assignee: POLA CHEMICAL INDUSTRIES, INC., Shizuoka (JP)

( * ) Notice: Subject to any disclaimer, the term of this patent is extended or adjusted under 35 U.S.C. 154(b) by 591 days.

(21) Appl. No.: 17/057,320

(22) PCT Filed: Apr. 24, 2019

(86) PCT No.: PCT/JP2019/017350
§ 371 (c)(1),
(2) Date: Nov. 20, 2020

(87) PCT Pub. No.: WO2019/230274
PCT Pub. Date: Dec. 5, 2019

(65) Prior Publication Data
US 2021/0196599 A1    Jul. 1, 2021

(30) Foreign Application Priority Data
May 29, 2018 (JP) ................. 2018-101963

(51) Int. Cl.
*A61K 8/44* (2006.01)
*A61Q 19/02* (2006.01)

(52) U.S. Cl.
CPC ........... *A61K 8/44* (2013.01); *A61Q 19/02* (2013.01); *A61K 2800/434* (2013.01)

(58) Field of Classification Search
None
See application file for complete search history.

(56) References Cited

U.S. PATENT DOCUMENTS

| | | | |
|---|---|---|---|
| 5,578,324 A | 11/1996 | Dohi et al. | |
| 5,719,197 A | 2/1998 | Kanios et al. | |
| 2004/0013741 A1* | 1/2004 | Meisel | A61K 31/135 514/540 |
| 2009/0098207 A1 | 4/2009 | Malakhov et al. | |
| 2010/0016442 A1 | 1/2010 | Cohen et al. | |
| 2010/0292509 A1 | 11/2010 | Kajiya et al. | |
| 2019/0388317 A1 | 12/2019 | Mori et al. | |

FOREIGN PATENT DOCUMENTS

| | | |
|---|---|---|
| EP | 0604667 A1 | 7/1994 |
| JP | S58-046049 A | 3/1983 |
| JP | S63-270650 A | 11/1988 |
| JP | H03-083912 A | 4/1991 |
| JP | 2008-110967 A | 5/2008 |
| JP | 2009-256329 A | 11/2009 |
| WO | WO 1994/02444 A1 | 2/1994 |
| WO | WO 95/03818 A1 | 2/1995 |
| WO | WO 2018/097274 A1 | 3/2018 |

OTHER PUBLICATIONS

Tanabe H, et al. A novel anti-ulcer agent (TEI-5103) acting directly on the gastric mucosa from lumen. II: Distribution of TEI-5103 to gastric mucosa in rats. Drug Metabolism and Pharmacokinetics, 1988, 3(1):33-40.*
Rotraxate, MedChem Express Product Data Sheet, 2024.*
International Search Report for PCT/JP2019/017350 mailed on Jul. 23, 2019.
Office Action issued in corresponding Indian Application No. 202017049997, dated Mar. 19, 2021.

* cited by examiner

*Primary Examiner* — David J Blanchard
*Assistant Examiner* — Sarah J Chickos
(74) *Attorney, Agent, or Firm* — Knobbe, Martens, Olson & Bear, LLP

(57) ABSTRACT

The object is to provide a skin whitening agent having an excellent skin whitening effect. A compound expressed by the following Formula (1), or an acid addition salt thereof is used as an active ingredient of the skin whitening agent:

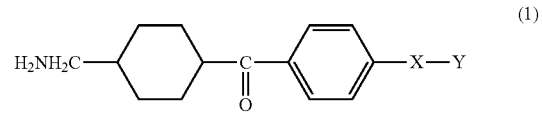

(1)

wherein, X represents an alkylene group having 1 to 2 carbon atoms, where a hydrogen atom may be substituted with a methyl group; Y represents $COOR^1$ or $CH_2OR^2$; $R^1$ represents a hydrogen atom, or an optionally branched alkyl group having 1 to 6 carbon atoms; and $R^2$ represents a hydrogen atom or an optionally branched acyl group having 1 to 6 carbon atoms.

3 Claims, No Drawings

SKIN LIGHTENING AGENT

TECHNICAL FIELD

The present invention relates to a skin whitening agent having an excellent skin whitening effect.

BACKGROUND ART

Skin manifestation caused by pigmentation, such as blemish, freckle, liver spot, and melanosis caused by a drug, in addition to sunburn caused by exposure to UV light, is known to develop when melanin production in pigment cells (melanocytes) increases, and the produced melanin pigments are deposited in the skin due to abnormal turnover, or the like.

Such skin manifestation associated with pigmentation is easily recognized from the appearance, and therefore has a significant impact on the face impression. For this reason, interest in the prevention or amelioration of skin pigmentation is quite strong especially among those having a desire to make their skin look beautiful, and there has been a great demand in recent years for a skin whitening agent, and cosmetics for skin whitening.

Ascorbic acid, hydroquinone, etc. have long been known as a skin whitening agent for prevention or amelioration of skin pigmentation, and external preparations for skin containing these agents have been widely used for prevention or amelioration of skin pigmentation. Further, since the action mechanism by which pigmentation occurs has been recently elucidated, development of skin whitening agents, such as a melanin production inhibitor, a tyrosinase inhibitor, a tyrosinase gene expression inhibitor, an α-MSH inhibitor, an antioxidant, a melanocyte dendrite extension inhibitor, and an inhibitor of melanosome delivery from melanocytes to keratinocytes, based on the action mechanism different from conventional skin whitening agents, has been actively conducted.

However, heretofore developed skin whitening agents have not been fully satisfactory, although a certain skin whitening effect may be recognized, or they may sometimes cause another undesired effect (side effect) at a concentration where a skin whitening effect can be exerted. Therefore, there is a demand for a new ingredient that has high safety and exhibits excellent skin whitening effect, and research and development therefor are underway.

Cetraxate or its salt is a compound that is one of the active ingredients for a skin whitening agent having been recently developed, which is degraded by metabolism to tranexamic acid (Patent Literature 1). Tranexamic acid is known to exhibit an inhibitory effect on production of prostaglandin E2 which activates melanocytes, and an inhibitory effect on tyrosinase, so as to provide a skin whitening effect. It has been reported that cetraxate exhibits a skin whitening effect by the activity of the compound itself, in addition to the skin whitening effect of tranexamic acid which is a metabolite of cetraxate.

In this regard, it has been confirmed that the aminocarboxylic acid derivative described in Patent Literature 2 has an antiulcer effect, and its use as a pharmaceutical product has been proposed. Incidentally, the structure of the compound partially agrees with that of tranexamic acid.

CITATION LIST

Patent Literature

[Patent Literature 1] Japanese Patent Application Laid-Open No. 2008-110967

[Patent Literature 2] Japanese Examined Patent Publication No. 64-4508

SUMMARY OF INVENTION

Technical Problem

An object of the present invention is to provide a skin whitening agent having high safety and excellent skin whitening effect.

Solution to Problem

The present inventors diligently conducted studies in search of a compound having a skin whitening effect to find that an aminocarboxylic acid derivative and an acid addition salt thereof having a specific structure exhibited excellent skin whitening effect, thereby completing the present invention.

That is, an aspect of the present invention is a skin whitening agent comprising a compound expressed by the following Formula (1), or an acid addition salt thereof.

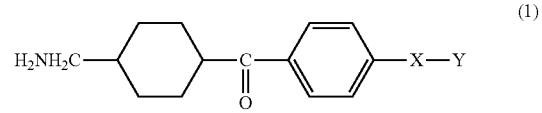

(Wherein, X represents an alkylene group having 1 to 2 carbon atoms, where a hydrogen atom may be substituted with a methyl group; Y represents $COOR^1$ or $CH_2OR^2$; $R^1$ represents a hydrogen atom, or an optionally branched alkyl group having 1 to 6 carbon atoms; and $R^2$ represents a hydrogen atom or an optionally branched acyl group having 1 to 6 carbon atoms.)

Another aspect of the present invention is a skin external composition for skin whitening comprising the above skin whitening agent. The skin external composition is preferably a cosmetic.

Advantageous Effects of Invention

The present invention provides a skin whitening agent having an excellent skin whitening effect. In addition, a skin external composition for skin whitening comprising the skin whitening agent is also provided, which is suitable as a cosmetic.

DESCRIPTION OF EMBODIMENTS

The skin whitening agent of the present invention contains a compound expressed by the following Formula (1) or an acid addition salt thereof.

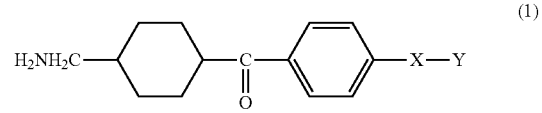

In Formula (1), X represents an alkylene group having 1 to 2 carbon atoms, in which a hydrogen atom may be substituted with a methyl group. The alkylene group having 1 to 2 carbon atoms is a methylene group, and an ethylene group. X is preferably —$CH_2$—$CH(CH_3)$—, or —$CH_2$—$CH_2$—.

In Formula (1), Y represents $COOR^1$ or $CH_2OR^2$, $R^1$ represents a hydrogen atom, or an optionally branched alkyl group having 1 to 6 carbon atoms, and $R^2$ represents a hydrogen atom, or an optionally branched acyl group having 1 to 6 carbon atoms.

That is, in a case where Y is $COOR^1$, when $R^1$ is a hydrogen atom, Y is a carboxyl group; and when $R^1$ is an optionally branched alkyl group having 1 to 6 carbon atoms, Y is an ester group. Examples of the optionally branched alkyl group having 1 to 6 carbon atoms include a methyl group, an ethyl group, a n-propyl group, an isopropyl group, a n-butyl group, an isobutyl group, a tert-butyl group, a n-pentyl group, and a n-hexyl group. From the viewpoint of skin whitening effect, $R^1$ is particularly preferably a hydrogen atom, and when $R^1$ is an alkyl group, it is more preferable that the carbon number thereof is small.

Also, in a case where Y is $CH_2OR^2$, when $R^2$ is a hydrogen atom, Y is a hydroxymethyl group; and when $R^2$ is an optionally branched acyl group having 1 to 6 carbon atoms, Y is an ester group. Examples of the optionally branched acyl group having 1 to 6 carbon atoms include a formyl group, an acetyl group, an acryloyl group, a propionyl group, a propioloyl group, a butyryl group, an isobutyryl group, a methacryloyl group, a valeryl group, and a caproyl group. From the viewpoint of skin whitening effect, $R^2$ is particularly preferably a hydrogen atom, and when $R^2$ is an acyl group, it is more preferable that the carbon number thereof is small.

In Formula (1), the conformation of the 1,4-cyclohexylene group may be either of the chair shape and the boat shape. Also, the two bonds may be in either cis or trans relationship. Preferably, they are in the trans relationship with a chair shape conformation.

Examples of an acid addition salt of the compound expressed by the following Formula (1) include salts with an inorganic acid, an organic carboxylic acid, or an organic sulfonic acid. Examples of the inorganic acid include hydrochloric acid, hydrobromic acid, sulfuric acid, nitric acid, and phosphoric acid. Examples of the organic carboxylic acid include acetic acid, propionic acid, maleic acid, fumaric acid, oxalic acid, citric acid, butyric acid, lactic acid, and tartaric acid. Examples of the organic sulfonic acid include methanesulfonic acid, ethanesulfonic acid, benzenesulfonic acid, and p-toluenesulfonic acid. Among them, the inorganic acid salt is preferable, and a hydrochloride salt is more preferable.

As an active ingredient of the skin whitening agent of the present invention, any of compounds expressed by Formula (1) or acid addition salts thereof may be used, however, the acid addition salts are more preferable.

Specific examples of the compound expressed by Formula (1) are listed below, but needless to say, the compound is not limited thereto.

2-[p-(4-aminomethylcyclohexylcarbonyl)phenyl]acetic acid, methyl 2-[p-(4-aminomethylcyclohexylcarbonyl)phenyl]acetate, ethyl 2-[p-(4-aminomethylcyclohexylcarbonyl)phenyl]acetate, propyl 2-[p-(4-aminomethylcyclohexylcarbonyl)phenyl]acetate, butyl 2-[p-(4-aminomethylcyclohexylcarbonyl)phenyl]acetate, pentyl 2-[p-(4-aminomethylcyclohexylcarbonyl)phenyl]acetate, hexyl 2-[p-(4-aminomethylcyclohexylcarbonyl)phenyl]acetate;

2-[p-(4-aminomethylcyclohexylcarbonyl)phenyl]ethanol, 2-[p-(4-aminomethylcyclohexylcarbonyl)phenyl]ethyl formate, 2-[p-(4-aminomethylcyclohexylcarbonyl)phenyl]ethyl acetate, 2-[p-(4-aminomethylcyclohexylcarbonyl)phenyl]ethyl propionate, 2-[p-(4-aminomethylcyclohexylcarbonyl)phenyl]ethyl butyrate, 2-[p-(4-aminomethylcyclohexylcarbonyl)phenyl]ethyl pentanoate, 2-[p-(4-aminomethylcyclohexylcarbonyl)phenyl]ethyl hexanoate;

2-[p-(4-aminomethylcyclohexylcarbonyl)phenyl]propionic acid, methyl 2-[p-(4-aminomethylcyclohexylcarbonyl)phenyl]propionate, ethyl 2-[p-(4-aminomethylcyclohexylcarbonyl)phenyl]propionate, propyl 2-[p-(4-aminomethylcyclohexylcarbonyl)phenyl]propionate, butyl 2-[p-(4-aminomethylcyclohexylcarbonyl)phenyl]propionate, pentyl 2-[p-(4-aminomethylcyclohexylcarbonyl)phenyl]propionate, hexyl 2-[p-(4-aminomethylcyclohexylcarbonyl)phenyl]propionate;

2-[p-(4-aminomethylcyclohexylcarbonyl)phenyl]propanol, 2-[p-(4-aminomethylcyclohexylcarbonyl)phenyl]propyl formate, 2-[p-(4-aminomethylcyclohexylcarbonyl)phenyl]propyl acetate, 2-[p-(4-aminomethylcyclohexylcarbonyl)phenyl]propyl propionate, 2-[p-(4-aminomethylcyclohexylcarbonyl)phenyl]propyl butyrate, 2-[p-(4-aminomethylcyclohexylcarbonyl)phenyl]propyl pentanoate, 2-[p-(4-aminomethylcyclohexylcarbonyl)phenyl]propyl hexanoate;

3-[p-(4-aminomethylcyclohexylcarbonyl)phenyl]propionic acid (compound 1), 3-[p-(4-aminomethylcyclohexylcarbonyl)phenyl]propionate methyl, 3-[p-(4-aminomethylcyclohexylcarbonyl)phenyl]propionate ethyl, 3-[p-(4-aminomethylcyclohexylcarbonyl)phenyl]propionate propyl, 3-[p-(4-aminomethylcyclohexylcarbonyl)phenyl]propionate butyl, 3-[p-(4-aminomethylcyclohexylcarbonyl)phenyl]propionate pentyl, 3-[p-(4-aminomethylcyclohexylcarbonyl)phenyl]propionate hexyl (compound 2);

3-[p-(4-aminomethylcyclohexylcarbonyl)phenyl]propanol (compound 3), 3-[p-(4-aminomethylcyclohexylcarbonyl)phenyl]propyl formate, 3-[p-(4-aminomethylcyclohexylcarbonyl)phenyl]propyl acetate, 3-[p-(4-aminomethylcyclohexylcarbonyl)phenyl]propyl propionate, 3-[p-(4-aminomethylcyclohexylcarbonyl)phenyl]propyl butyrate, 3-[p-(4-aminomethylcyclohexylcarbonyl)phenyl]propyl pentanoate, 3-[p-(4-aminomethylcyclohexylcarbonyl)phenyl]propyl hexanoate (compound 4);

2-methyl-3-[p-(4-aminomethylcyclohexylcarbonyl)phenyl]propanol, 2-methyl-3-[p-(4-aminomethylcyclohexylcarbonyl)phenyl]propyl formate, 2-methyl-3-[p-(4-aminomethylcyclohexylcarbonyl)phenyl]propyl acetate, 2-methyl-3-[p-(4-aminomethylcyclohexylcarbonyl)phenyl]propyl propionate, 2-methyl-3-[p-(4-aminomethylcyclohexylcarbonyl)phenyl]propyl butyrate, 2-methyl-3-[p-(4-aminomethylcyclohexylcarbonyl)phenyl]propyl pentanoate, and 2-methyl-3-[p-(4-aminomethylcyclohexylcarbonyl)phenyl]propyl hexanoate (compound 5).

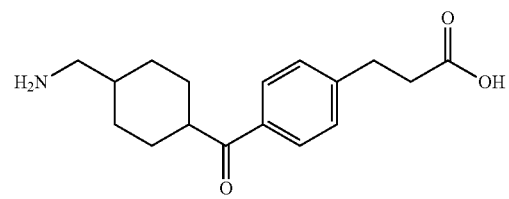

(Compound 1)

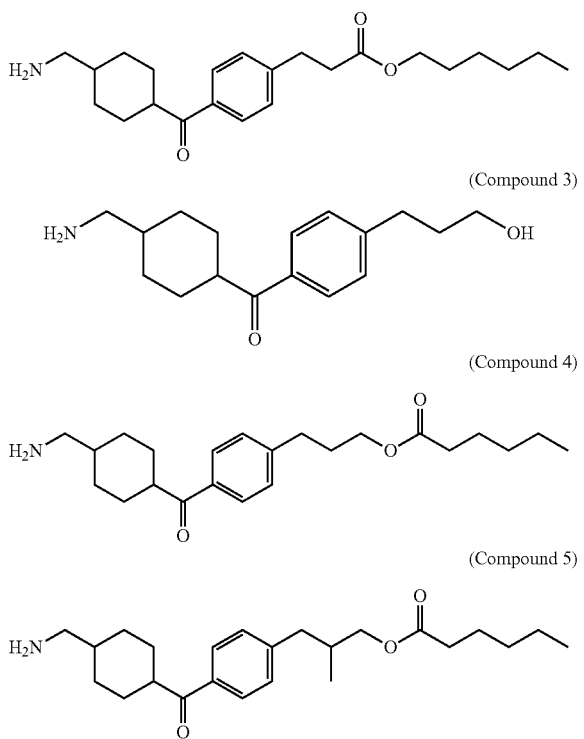

(Compound 2)
(Compound 3)
(Compound 4)
(Compound 5)

The compound expressed by Formula (1) can be obtained through synthesis and purification according to conventional methods. For example, it can be synthesized by an acylation reaction in the presence of a Lewis acid of an acid addition salt of an aminocarboxylic acid halide described in Patent Literature 2, and then through a suitable isolation and purification method.

Since the compound expressed by Formula (1) or an acid addition salt thereof has an excellent skin whitening effect, the same constitutes an active ingredient of a skin whitening agent.

In this regard, skin whitening means herein prevention and/or amelioration of pigmentation, and more specifically prevention and/or amelioration of pigmentation symptoms caused by production enhancement, excessive accumulation, abnormal deposit or the like of melanin, such as blemish, dullness, freckle, sunburn, or darkening of skin caused by inflammation or irritation, as well as pigmentation symptoms caused by a disease causing pigmentation, such as skin melanosis due to a drug such as steroids.

Although the action mechanism of the skin whitening agent of the present invention is not very clear, it is conjectured that prevention and/or amelioration of pigmentation is induced by a tyrosinase activity inhibition effect, such as a tyrosinase inhibition effect, a tyrosinase gene expression inhibition effect, a tyrosinase protein expression inhibition effect, or a degradation effect on a tyrosinase associated protein, a proton pump inhibition effect, an inhibition effect on melanosome delivery from melanocytes to keratinocytes, or a novel action mechanism.

From another viewpoint, the present invention may be understood as a method of skin whitening, or a method of preventing and/or ameliorating pigmentation comprising application of a compound expressed by Formula (1) or an acid addition salt thereof.

From another viewpoint, the present invention may be understood as a use of a compound expressed by Formula (1) or an acid addition salt thereof for skin whitening, or for preventing and/or ameliorating pigmentation.

From another viewpoint, the present invention may be understood as a use of a compound expressed by Formula (1) or an acid addition salt thereof for producing a skin whitening agent.

From another viewpoint, the present invention may be understood as a compound expressed by Formula (1) or an acid addition salt thereof used for skin whitening, or for preventing and/or ameliorating pigmentation.

The structure of a compound expressed by Formula (1) partially agrees with that of tranexamic acid, however it has been known that that the compound is not metabolized to tranexamic acid in vivo. That is, the skin whitening effect of the compound expressed by Formula (1) is thought to be due to a mechanism different from that with the tranexamic acid. It is presumed that at least the structure of (4-aminomethylcyclohexylcarbonyl)phenyl group participates in development of the effect.

Cetraxate described in Patent Literature 1 is an ester derivative of tranexamic acid, which exerts a skin whitening effect by its own structure, and by cleavage of the ester bond by metabolism to tranexamic acid.

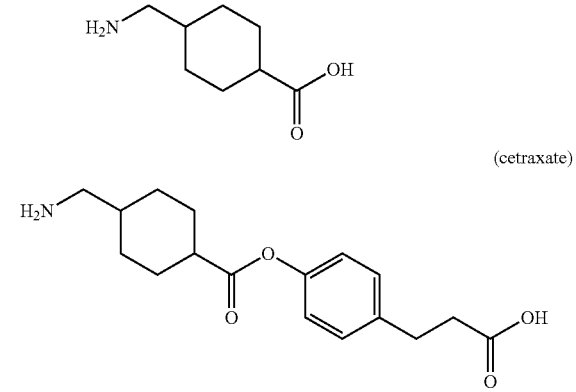

(tranexamic acid)

(cetraxate)

A skin whitening agent of the present invention may be contained in a composition for skin whitening, and particularly preferably in an external composition for skin, from which an effect can be expected by percutaneous absorption. There is no particular restriction on the form of the external composition for skin, insofar as it can be applied to the skin externally, and preferable examples thereof include a cosmetic (including a quasi-drug), and medicinal products. Since high safety has been confirmed with respect to the compounds expressed by Formula (1), the same may be continuously applied in the form of a cosmetic which is routinely used.

There is no particular restriction on the formulation of the external composition for skin, and examples thereof include a lotion formulation, an emulsion formulation, such as milky lotion or cream, an oil formulation, a gel formulation, a pack, and a cleanser.

In a case where a skin whitening agent of the present invention is blended in a skin external composition for skin whitening, when the amount thereof with respect to the total amount of the composition is preferably from 0.01% to 20% by mass, more preferably from 0.1 to 10% by mass, and further preferably from 1 to 5% by mass, a desired effect can be easily obtained, and the design flexibility of the recipe can be secured.

A skin external composition for skin whitening according to the present invention may optionally contain ingredients to be incorporated commonly in an external composition for skin in addition to a skin whitening agent of the present invention to the extent that the advantageous effects of invention are not impaired.

Examples of such ingredients include an oil and wax, such as a macadamia nut oil, an avocado oil, a corn oil, an olive oil, a rapeseed oil, a sesame oil, a castor oil, a safflower oil, a cottonseed oil, a jojoba oil, a coconut oil, a palm oil, a liquid lanolin, a hydrogenated coconut oil, a hydrogenated oil, a Japan wax, a hydrogenated castor oil, a bees wax, a candelilla wax, a carnauba wax, an insect wax, lanolin, a reduced lanolin, a hard lanolin, and a jojoba wax; a hydrocarbon, such as liquid paraffin, squalane, pristane, ozokerite, paraffin, ceresin, petrolatum, and a microcrystalline wax; a higher fatty acid, such as oleic acid, isostearic acid, lauric acid, myristic acid, palmitic acid, stearic acid, behenic acid, and undecylenic acid; a higher alcohol, such as cetyl alcohol, stearyl alcohol, isostearyl alcohol, behenyl alcohol, octyldodecanol, myristyl alcohol, and cetostearyl alcohol; a synthetic ester oil, such as cetyl isooctanoate, isopropyl myristate, hexyldecyl isostearate, diisopropyl adipate, di-2-ethylhexyl sebacate, cetyl lactate, diisostearyl malate, ethylene glycol di-2-ethylhexanoate, neopentyl glycol dicaprate, glycerol di-2-heptylundecanoate, glycerol tri-2-ethylhexanoate, trimethylolpropane tri-2-ethylhexanoate, trimethylolpropane triisostearate, and pentaerythrityl tetra-2-ethylhexanoate; an open-chain polysiloxane, such as dimethylpolysiloxane, methylphenylpolysiloxane, and diphenylpolysiloxane; a cyclic polysiloxane, such as octamethylcyclotetrasiloxane, decamethylcyclopentasiloxane, and dodecamethylcyclohexasiloxane; and an oil like a silicone oil as a modified polysiloxane, such as an amino-modified polysiloxane, a polyether-modified polysiloxane, an alkyl-modified polysiloxane, and a fluorine-modified polysiloxane;

An anionic surfactant, such as fatty acid soap (sodium laurate, sodium palmitate, etc.), potassium lauryl sulfate, and triethanolamine alkyl ether sulfate; a cationic surfactant, such as stearyl trimethyl ammonium chloride, benzalkonium chloride, and lauryl amine oxide; an amphoteric surfactant, such as an imidazoline type amphoteric surfactant (2-cocoyl-2-imidazolinium hydroxide-1-carboxyethyloxy disodium salt, etc.), a betaine type surfactant (alkylbetaine, amidobetaine, sulfobetaine, etc.), and acylmethyltaurine; a nonionic surfactant, such as a sorbitan fatty acid ester (sorbitan monostearate, sorbitan sesquioleate, etc.), a glycerol fatty acid (glycerol monostearate, etc.), a propylene glycol fatty acid ester (propylene glycol monostearate, etc.), a hydrogenated castor oil derivative, a glycerol alkyl ether, a POE sorbitan fatty acid ester (POE sorbitan monooleate, polyoxyethylene sorbitan monostearate, etc.), a POE sorbit fatty acid ester (POE-sorbit monolaurate, etc.), a POE glycerol fatty acid ester (POE glycerol monoisostearate, etc.), a POE fatty acid ester (poly(ethylene glycol) monooleate, POE distearate, etc.), a POE alkyl ether (POE 2-octyldodecyl ether, etc.), a POE alkylphenyl ether (POE nonylphenyl ether, etc.), Pluronic series, a POE·POP alkyl ether (POE·POP 2-decyltetradecyl ether, etc.), Tetronic series, a POE castor oil or hydrogenated castor oil derivative (POE castor oil, POE hydrogenated castor oil, etc.), a sucrose fatty acid ester, and an alkyl glucoside; a polyhydric alcohol, such as poly(ethylene glycol), glycerol, 1,3-butylene glycol, erythritol, sorbitol, xylitol, maltitol, propylene glycol, dipropylene glycol, diglycerol, isoprene glycol, 1,2-pentanediol, 2,4-hexanediol, 1,2-hexanediol, and 1,2-octanediol;

A moisturizing component, such as sodium pyrrolidone carboxylate, lactic acid, and sodium lactate; a powder, which may be optionally surface-treated, such as mica, talc, kaolin, synthetic mica, calcium carbonate, magnesium carbonate, anhydrous silicic acid (silica), aluminum oxide, and barium sulfate; an inorganic pigment, which may be optionally surface-treated, such as Bengal red, yellow iron oxide, black iron oxide, cobalt oxide, ultramarine blue, iron blue, titanium oxide, and zinc oxide; a pearling agent, which may be optionally surface-treated, such as titanated mica, fish scale flake, and bismuth oxychloride; an organic dye, which may be optionally laked, such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Violet No. 201, and Red No. 204; an organic powder, such as a polyethylene powder, poly(methyl methacrylate), a nylon powder, and an organopolysiloxane elastomer; a p-aminobenzoic acid type ultraviolet absorber; an anthranilic acid type ultraviolet absorber; a salicylic acid type ultraviolet absorber; a cinnamic acid type ultraviolet absorber; a benzophenone type ultraviolet absorber; a sugar type ultraviolet absorber; an ultraviolet absorber, such as 2-(2'-hydroxy-5'-t-octylphenyl)benzotriazole, and 4-methoxy-4'-t-butyldibenzoylmethane;

A lower alcohol, such as ethanol, and isopropanol; a vitamin B, such as vitamin A or its derivatives, vitamin $B_6$ or its derivatives, vitamin $B_6$ hydrochloride, vitamin $B_6$ tripalmitate, vitamin $B_6$ dioctanoate, vitamin $B_2$ or its derivatives, vitamin $B_{12}$, and vitamin $B_{15}$ or its derivatives; a vitamin, a vitamin E, such as α-tocopherol, β-tocopherol, γ-tocopherol, and vitamin E acetate; other vitamins, such as a vitamin D, vitamin H, pantothenic acid, pantethine, and pyrroloquinoline quinone; an antimicrobial agent (preservative), such as methylparaben, ethylparaben, butylparaben, and phenoxyethanol; an anti-inflammatory agent, such as a glycyrrhizic acid derivative, a glycyrrhetinic acid derivative, a salicylic acid derivative, hinokitiol, zinc oxide, and allantoin; a wrinkle improving agent, such as retinol, ascorbic acid, tocopherol, and farnesyl acetate; various extracts (e.g., Phellodendron bark, Coptis Rhizome, Lithospermi radix, peony root, swertia herb, birch, sage, loquat, carrot, aloe, mallow, iris, grape, coix seed, loofah, lily, saffron, cnidium rhizome, ginger, Hypericum, Ononis, garlic, Capsicum, Citrus Unshiu peel, Japanese Angelica root, and seaweed, etc.; an activator, such as royal jelly, a photosensitizer, and a cholesterol derivative; a blood circulation promoter, such as nonylic acid vanillylamide, capsaicin, zingelon, and tannic acid; an antiseborrheic agent, such as sulfur, and thianthol; an anti-inflammatory agent, such as tranexamic acid, thiotaurine, and hypotaurine; and a water-soluble polymer, such as collagen and hyaluronic acid.

A skin whitening agent other than the skin whitening agent of the present invention may be also blended together. Examples thereof include an alkylresorcinol, ascorbic acid and its derivative, a placenta extract, extracts of a plant, such as saxifrage and pearl barley, and arbutin.

EXAMPLES

The present invention will be described in more detail below with reference to concrete experimental examples, provided that the present invention is not limited to the following aspects.

<Test of Skin Whitening Effect>

The cosmetics according to Table 1 (Examples 1 to 9, Comparative Example, and Reference Example) were prepared respectively in a conventional manner.

With regard to each of the prepared cosmetics, the skin whitening effect (pigmentation ameliorating effect) was evaluated by the following method. That is, total 8 test sites in a size of 0.5 cm×0.5 cm were established on the medial parts of the left and right upper arms of each of 10 panelists who participated voluntarily. Each established site was irradiated with a minimum erythema dose (1 MED) of UV light once a day for three consecutive days, namely totally three times. At the end of the UV irradiation on the first day of the test (at the end of the first irradiation) and thereafter each 50 μL of the cosmetics of Comparative Example and any one of Examples 1 to 9 or Reference Example were applied respectively to one site and the remaining seven sites twice a day for 25 consecutive days. The skin lightness (L* value) of each test site was measured 24 hours after the end of the 25-day application period with a color difference meter (CR-300, Konica Minolta Holdings, Inc.). By subtracting the L* value of the site to which the cosmetic of Comparative Example was applied from each L* value of the sites to which the cosmetic of Example or Reference Example was applied, the difference in skin lightness (ΔL* value) was calculated. Since the L* value decreases, as the degree of pigmentation becomes severer, it may be so judged that pigmentation is ameliorated, when the ΔL* value is higher.

TABLE 1

|  | (% by mass) |
| --- | --- |
| POE (60) hydrogenated castor oil | 0.1 |
| 1,3-Butanediol | 5 |
| Glycerol | 2 |
| Poly(ethylene glycol) 400 | 3 |
| 1,2-Pentanediol | 3 |
| Potassium hydroxide | 0.005 |
| Methylparaben | 0.2 |
| Compound in Table 2 | Amount in Table 2 |
| Water | Balance |

TABLE 2

|  | Compound | Content (% by mass) | Pigmentation amelioration ΔL* | Rating[#] |
| --- | --- | --- | --- | --- |
| Example 1 | Hydrochloride of Compound 1 | 1 | 0.52 | AA |
| Example 2 | Compound 1 | 3 | 0.52 | AA |
| Example 3 | Compound 1 | 1 | 0.50 | AA |
| Example 4 | Compound 1 | 0.01 | 0.47 | A |
| Example 5 | Compound 3 | 1 | 0.48 | A |
| Example 6 | Compound 3 | 0.01 | 0.45 | A |
| Example 7 | Compound 2 | 1 | 0.43 | A |
| Example 8 | Compound 4 | 1 | 0.45 | A |
| Example 9 | Compound 5 | 1 | 0.42 | A |
| Comparative Example | None | 0 | — | — |
| Reference Example | Tranexamic acid | 1 | 0.40 | B |

[#]AA: ΔL* ≥ 0.5%, A: 0.4 < ΔL* < 0.5, B: ΔL* ≤ 0.4

Production Example 1

A cosmetic lotion which was an external preparation for skin of the present invention was prepared according to the recipe shown in Table 3. That is, the ingredients of A were mixed at room temperature, and the ingredients of B were heated at 60° C. respectively and mixed together, then B was gradually added to A with stirring, and the mixture was cooled with stirring to yield a cosmetic lotion.

It was confirmed that this cosmetic lotion gave a skin whitening effect when applied to the skin.

TABLE 3

| Cosmetic lotion | | |
| --- | --- | --- |
|  |  | (% by mass) |
| A | Poly(ethylene glycol) | 0.5 |
|  | Glycerol | 10.0 |
|  | Pentylene glycol | 2.0 |
|  | Ethanol | 5.0 |
|  | Diglycerol | 1.0 |
|  | Citric acid | 0.1 |
|  | Sodium citrate | 0.1 |
|  | Methylparaben | 0.2 |
|  | Phenoxyethanol | 0.2 |
|  | Pentasodium pentetate | 0.1 |
|  | Xanthan gum | 0.1 |
|  | Hydrochloride salt of Compound 1 | 1.0 |
|  | Water | Balance |
| B | 1.3-Butylene glycol | 5.0 |
|  | PEG-60 Hydrogenated castor oil | 0.1 |
|  | Sucrose laurate | 0.2 |
|  | Perfume | 0.2 |
|  | Total | 100.0 |

Production Example 2

A cosmetic lotion which was an external preparation for skin of the present invention was prepared according to the recipe shown in Table 4. That is, the ingredients of A were mixed at room temperature, and the ingredients of B were heated at 60° C. respectively and mixed together, then B was gradually added to A with stirring, and the mixture was cooled with stirring to yield a cosmetic lotion.

It was confirmed that this cosmetic lotion gave a skin whitening effect when applied to the skin.

TABLE 4

| Cosmetic lotion | | |
| --- | --- | --- |
|  |  | (% by mass) |
| A | Poly (ethylene glycol) | 0.5 |
|  | Glycerol | 10.0 |
|  | Pentylene glycol | 2.0 |
|  | Ethanol | 5.0 |
|  | Diglycerol | 1.0 |
|  | Citric acid | 0.1 |
|  | Sodium citrate | 0.1 |
|  | Methylparaben | 0.2 |
|  | Phenoxyethanol | 0.2 |
|  | Pentasodium pentetate | 0.1 |
|  | Xanthan gum | 0.1 |
|  | Hydrochloride salt of Compound 1 | 1.0 |
|  | Water | Balance |
| B | 1,3-Butylene glycol | 5.0 |
|  | PEG-60 Hydrogenated castor oil | 0.2 |
|  | Sucrose laurate | 0.2 |
|  | Glycerol tri(2-ethylhexanoate) | 1.0 |
|  | Perfume | 0.2 |
|  | Total | 100.0 |

Production Example 3

An essence which was an external preparation for skin of the present invention was prepared according to the recipe shown in Table 5. That is, the ingredients of A and B were heated at 80° C. respectively, and mixed together, then B was gradually added to A with stirring, and the mixture was cooled with stirring to yield an essence.

It was confirmed that this essence gave a skin whitening effect when applied to the skin.

TABLE 5

| | Essence | |
|---|---|---|
| | | (% by mass) |
| A | Poly(ethylene glycol) | 0.5 |
| | Glycerol | 10.0 |
| | Pentylene glycol | 2.0 |
| | Ethanol | 5.0 |
| | Diglycerol | 1.0 |
| | Citric acid | 0.1 |
| | Sodium citrate | 0.1 |
| | Potassium hydroxide | 0.1 |
| | Methylparaben | 0.2 |
| | Phenoxyethanol | 0.2 |
| | Pentasodium pentetate | 0.1 |
| | Arbutin | 3.0 |
| | Carbomer | 0.2 |
| | Xanthan gum | 0.1 |
| | Hydrochloride salt of Compound 1 | 1.0 |
| | Dipotassium glycyrrhizinate | 0.1 |
| | Water | Balance |
| B | 1,3-Butylene glycol | 5.0 |
| | PEG-60 Hydrogenated castor oil | 0.1 |
| | Sucrose laurate | 0.2 |
| | Perfume | 0.2 |
| | Total | 100.0 |

Production Example 4

A milky lotion which was an external preparation for skin of the present invention was prepared according to the recipe shown in Table 6. That is, the ingredients of A and B were heated at 80° C. respectively, and mixed together, then B was gradually added to A with stirring, and the mixture was cooled with stirring to yield a milky lotion.

It was confirmed that this milky lotion gave a skin whitening effect when applied to the skin.

TABLE 6

| | Milky lotion | |
|---|---|---|
| | | (% by mass) |
| A | Poly(ethylene glycol) | 0.5 |
| | 1,3-Butylene glycol | 5.0 |
| | Glycerol | 10.0 |
| | Pentylene glycol | 2.0 |
| | Ethanol | 5.0 |
| | Diglycerol | 1.0 |
| | Citric acid | 0.1 |
| | Sodium citrate | 0.1 |
| | Potassium hydroxide | 0.05 |
| | Calcium chloride | 0.02 |
| | Methylparaben | 0.2 |
| | Phenoxyethanol | 0.2 |
| | Pentasodium pentetate | 0.1 |
| | Arbutin | 3.0 |
| | Xanthan gum | 0.05 |
| | (Acrylate/(C10-30) alkyl acrylate) crosspolymer | 0.2 |
| | Propylene glycol alginate | 0.5 |
| | Fermented liquor of royal jelly | 0.5 |
| | Hydrochloride salt of Compound 1 | 1.0 |
| | Dipotassium glycyrrhizinate | 0.1 |
| | Water | Balance |
| B | Mineral oil | 1.0 |
| | Petrolatum | 0.5 |
| | Microcrystalline wax | 0.5 |
| | Cetyl ethylhexanoate | 1.0 |
| | Glyceryl trioctanoate | 1.0 |
| | Beeswax | 0.5 |
| | Dimethicone | 0.5 |
| | Methylphenylpolysiloxane | 0.5 |
| | Sorbitan stearate | 0.1 |
| | POE (20) sorbitan stearate | 0.1 |
| | PEG-25 stearate | 0.1 |
| | Sucrose stearate | 0.1 |
| | Stearic acid | 0.1 |
| | Cetanol | 0.5 |
| | Perfume | 0.2 |
| | Total | 100.0 |

Production Example 5

An O/W cream which was an external preparation for skin of the present invention was prepared according to the recipe shown in Table 7. That is, the ingredients of A and B were heated at 80° C. respectively, and mixed together, then B was gradually added to A with stirring, and the mixture was cooled with stirring to yield an O/W cream.

It was confirmed that this O/W cream gave a skin whitening effect when applied to the skin.

TABLE 7

| | O/W cream | |
|---|---|---|
| | | (% by mass) |
| A | Poly(ethylene glycol) | 0.5 |
| | 1,3-Butylene glycol | 5.0 |
| | Glycerol | 10.0 |
| | Pentylene glycol | 2.0 |
| | Ethanol | 2.0 |
| | Diglycerol | 1.0 |
| | Citric acid | 0.1 |
| | Sodium citrate | 0.1 |
| | Potassium hydroxide | 0.4 |
| | Methylparaben | 0.2 |
| | Phenoxyethanol | 0.2 |
| | Pentasodium pentetate | 0.1 |
| | Ascorbic acid glucoside | 2.0 |
| | Xanthan gum | 0.05 |
| | (Acrylate/(C10-30) alkyl acrylate) crosspolymer | 0.2 |
| | Hydrochloride salt of Compound 1 | 1.0 |
| | Dipotassium glycyrrhizinate | 0.1 |
| | Water | Balance |
| B | Mineral oil | 1.0 |
| | Petrolatum | 0.5 |
| | Microcrystalline wax | 0.5 |
| | Cetyl ethylhexanoate | 1.0 |
| | Glyceryl trioctanoate | 1.0 |
| | Beeswax | 0.5 |
| | Dimethicone | 0.5 |
| | Methylphenyl polysiloxane | 0.5 |
| | Sorbitan stearate | 0.5 |
| | POE-20 sorbitan stearate | 0.5 |
| | PEG-25 stearate | 0.5 |

TABLE 7-continued

| O/W cream | |
|---|---|
| | (% by mass) |
| Sucrose stearate | 0.5 |
| Stearic acid | 0.5 |
| Cetanol | 1.0 |
| Behenyl alcohol | 0.5 |
| Ethylhexylglycerin | 0.2 |
| Tocopherol | 0.1 |
| Perfume | 0.2 |
| Total | 100.0 |

Production Example 6

A W/O cream which was an external preparation for skin of the present invention was prepared according to the recipe shown in Table 8. That is, the ingredients of A and B were heated at 80° C. respectively, and mixed together, then A was gradually added to B with stirring, and the mixture was cooled with stirring to yield a W/O cream.

It was confirmed that this W/O cream gave a skin whitening effect when applied to the skin.

TABLE 8

| | W/O cream | |
|---|---|---|
| | | (% by mass) |
| A | Poly(ethylene glycol) | 0.5 |
| | 1,3-Butylene glycol | 5.0 |
| | Glycerol | 15.0 |
| | Pentylene glycol | 2.0 |
| | Ethanol | 2.0 |
| | Diglycerol | 1.0 |
| | Citric acid | 0.1 |
| | Sodium citrate | 0.1 |
| | Methylparaben | 0.2 |
| | Phenoxyethanol | 0.2 |
| | Pentasodium pentetate | 0.1 |
| | Ascorbic acid glucoside | 2.0 |
| | Hydrochloride salt of Compound 1 | 1.0 |
| | Dipotassium glycyrrhizinate | 0.1 |
| | Water | Balance |
| B | Mineral oil | 1.0 |
| | Petrolatum | 0.5 |
| | Microcrystalline wax | 0.5 |
| | Cetyl ethylhexanoate | 1.0 |
| | Glyceryl trioctanoate | 1.0 |
| | Beeswax | 0.5 |
| | Dimethicone | 0.5 |
| | Methylphenylpolysiloxane | 0.5 |
| | Decamethylcyclopentasiloxane | 27.2 |
| | Sucrose stearate | 0.5 |
| | PEG-10 dimethicone | 4.0 |
| | Dimethyl distearyl ammonium hectorite | 2.0 |
| | Ethylhexylglycerin | 0.2 |
| | Tocopherol | 0.1 |
| | Perfume | 0.2 |
| | Total | 100.0 |

Production Example 7

An O/W foundation which was an external preparation for skin of the present invention was prepared according to the recipe shown in Table 9. That is, the ingredients of A and B were heated at 80° C. respectively, and mixed together, then B was gradually added to A with stirring, and the mixture was cooled with stirring to yield an O/W foundation.

It was confirmed that this O/W foundation gave a skin whitening effect when applied to the skin.

TABLE 9

| | O/W foundation | |
|---|---|---|
| | | (% by mass) |
| A | Poly(ethylene glycol) | 0.5 |
| | 1,3-Butylene glycol | 2.0 |
| | Glycerol | 1.0 |
| | Pentylene glycol | 2.0 |
| | Ethanol | 1.0 |
| | Diglycerol | 0.5 |
| | Citric acid | 0.1 |
| | Sodium citrate | 0.1 |
| | Potassium hydroxide | 0.4 |
| | Triethanolamine | 0.4 |
| | Methylparaben | 0.2 |
| | Phenoxyethanol | 0.2 |
| | Pentasodium pentetate | 0.1 |
| | Phenylbenzimidazole sulfonic acid | 0.5 |
| | Ascorbic acid glucoside | 2.0 |
| | Xanthan gum | 0.1 |
| | Quince seed extract | 2.0 |
| | Golden silk extract | 0.5 |
| | Lotus extract | 0.5 |
| | Royal jelly fermented liquor | 0.5 |
| | Hydrochloride salt of Compound 1 | 1.0 |
| | Water | Balance |
| B | Mineral oil | 5.0 |
| | Petrolatum | 1.0 |
| | Microcrystalline wax | 1.0 |
| | Cetyl ethylhexanoate | 5.0 |
| | Glyceryl trioctanoate | 1.0 |
| | Hydrogenated rape oil | 1.0 |
| | Beeswax | 1.0 |
| | Dimethicone | 0.5 |
| | Methylphenyl polysiloxane | 0.5 |
| | Decamethylcyclopentasiloxane | 3.0 |
| | Crosslinked dimethicone | 0.5 |
| | t-Butyl methoxydibenzoylmethane | 1.0 |
| | Ethylhexyl methoxycinnamate | 1.0 |
| | Glyceryl oleate | 0.5 |
| | Polyglyceryl oleate | 0.5 |
| | Sorbitan isostearate | 1.0 |
| | PEG-20 stearate | 0.5 |
| | Sucrose stearate | 0.5 |
| | Polyoxyethylene phytostanol | 0.5 |
| | Polyoxyethylene polyglycerol stearyl ether | 0.5 |
| | Stearic acid | 1.5 |
| | Cetanol | 2.0 |
| | Behenyl alcohol | 1.0 |
| | (Alkyl acrylate/dimethicone) copolymer-treated and oxidized titanium | 9.0 |
| | (Alkyl acrylate/dimethicone) copolymer-treated and oxidized Bengal red | 1.0 |
| | (Alkyl acrylate/dimethicone) copolymer-treated and oxidized yellow iron oxide | 3.0 |
| | (Alkyl acrylate/dimethicone) copolymer-treated and oxidized black iron oxide | 0.1 |
| | Red No. 226 | 0.01 |
| | Safflower red | 0.01 |
| | Gardenia yellow | 0.01 |
| | Gem Tone Ruby (produced by Engelhard Corp.) | 0.2 |
| | Timiron Splendid Gold (produced by Merck & Co., Inc.) | 0.2 |
| | Reflecks Pinpoints of Pearl (produced by Engelhard Corp.) | 0.2 |
| | Trimethoxysilyl dimethicone-treated COLORONA GLITTER Bordeaux (produced by Merck & Co., Inc.) | 0.2 |
| | Trimethoxysilyl dimethicone-treated GENESTAR 420 (produced by Nihon Koken Kogyo Co., Ltd.) | 0.2 |
| | Trimethoxysilyl dimethicone-treated COVERLEAF MF (produced by JGC Catalysts and Chemicals Ltd.) | 0.2 |
| | Perfluorooctyltriethoxysilane-treated COVERLEAF PC1035 (produced by JGC Catalysts and Chemicals Ltd.) | 0.2 |
| | SILKYFLAKE FTD025FY-F02 (produced by Nippon Sheet Glass Co., Ltd.) | 0.2 |

TABLE 9-continued

O/W foundation

| | (% by mass) |
|---|---|
| METASHINE MT1080KY (produced by Nippon Sheet Glass Co., Ltd.) | 0.2 |
| Talc | 3.0 |
| Fine particle titanium oxide ("MT-100SA", produced by Tayca Corporation) | 2.0 |
| Fine particle zinc oxide | 1.0 |
| Ethylhexylglycerin | 0.2 |
| Tocopherol | 0.1 |
| Perfume | 0.2 |
| Total | 100.0 |

Production Example 8

A W/O foundation which was an external preparation for skin of the present invention was prepared according to the recipe shown in Table 10. That is, the ingredients of A and B were heated at 80° C. respectively, and mixed together, then A was gradually added to B with stirring, and the mixture was cooled with stirring to yield a W/O foundation.

It was confirmed that this W/O foundation gave a skin whitening effect when applied to the skin.

TABLE 10

W/O foundation

| | | (% by mass) |
|---|---|---|
| A | Poly (ethylene glycol) | 0.5 |
| | 1,3-Butylene glycol | 5.0 |
| | Glycerol | 1.0 |
| | Pentylene glycol | 2.0 |
| | Ethanol | 1.0 |
| | Diglycerol | 0.5 |
| | Citric acid | 0.1 |
| | Sodium citrate | 0.1 |
| | Potassium hydroxide | 0.4 |
| | Methylparaben | 0.2 |
| | Phenoxyethanol | 0.2 |
| | Pentasodium pentetate | 0.1 |
| | Phenylbenzimidazole sulfonic acid | 0.5 |
| | Ascorbic acid glucoside | 2.0 |
| | Xanthan gum | 0.1 |
| | Hydrochloride salt of Compound 1 | 1.0 |
| | Water | Balance |
| B | Mineral oil | 1.0 |
| | Petrolatum | 0.5 |
| | Microcrystalline wax | 0.5 |
| | Cetyl ethylhexanoate | 1.0 |
| | Glyceryl trioctanoate | 1.0 |
| | Beeswax | 0.5 |
| | Dimethicone | 0.5 |
| | Methylphenylpolysiloxane | 1.0 |
| | Decamethylcyclopentasiloxane | 14.0 |
| | Crosslinked dimethicone | 0.5 |
| | (Alkyl acrylate/dimethicone) copolymer | 0.5 |
| | Trimethylsiloxysilicate | 0.5 |
| | Caprylyl methicone | 0.5 |
| | t-Butyl methoxybenzoylmethane | 1.0 |
| | Ethylhexyl methoxycinnamate | 1.0 |
| | Glyceryl oleate | 0.5 |
| | Polyglyceryl oleate | 0.5 |
| | Sorbitan isostearate | 0.5 |
| | Sucrose stearate | 1.0 |
| | Polyoxyethylene polyglycerol stearyl ether | 0.5 |
| | PEG-10 dimethicone | 3.0 |
| | Dimethyl distearyl ammonium hectorite | 0.75 |
| | (Alkyl acrylate/dimethicone) copolymer-treated | 8.0 |

TABLE 10-continued

W/O foundation

| | (% by mass) |
|---|---|
| and oxidized titanium | |
| (Alkyl acrylate/dimethicone) copolymer-treated and oxidized Bengal red | 0.5 |
| (Alkyl acrylate/dimethicone) copolymer-treated and oxidized yellow iron oxide | 1.5 |
| (Alkyl acrylate/dimethicone) copolymer-treated and oxidized black iron oxide | 0.1 |
| Red No. 226 | 0.01 |
| Triethoxycaprylylsilane-treated Yellow No. 4 | 0.01 |
| Safflower red | 0.01 |
| Gardenia yellow | 0.01 |
| Gem Tone Ruby (produced by Engelhard Corp.) | 0.2 |
| Timiron Splendid Gold (produced by Merck & Co., Inc.) | 0.2 |
| Reflecks Pinpoints of Pearl (produced by Engelhard Corp.) | 0.2 |
| Trimethoxysilyl dimethicone-treated COLORONA GLITTER Bordeaux (produced by Merck & Co., Inc.) | 0.2 |
| Trimethoxysilyl dimethicone-treated GENESTAR 420 (produced by Nihon Koken Kogyo Co., Ltd.) | 0.2 |
| Trimethoxysilyl dimethicone-treated COVERLEAF MF (produced by JGC Catalysts and Chemicals Ltd.) | 0.2 |
| Perfluorooctyltriethoxysilane-treated COVERLEAF PC1035 (produced by JGC Catalysts and Chemicals Ltd.) | 0.2 |
| SILKYFLAKE FTD025FY-F02 (produced by Nippon Sheet Glass Co., Ltd.) | 0.2 |
| METASHINE MT1080KY (produced by Nippon Sheet Glass Co., Ltd.) | 0.2 |
| Talc | 3.0 |
| Fine particle titanium oxide ("MT-100SA", produced by Tayca Corporation) | 1.0 |
| Fine particle zinc oxide | 0.5 |
| Ethylhexylglycerin | 0.2 |
| Tocopherol | 0.1 |
| Perfume | 0.2 |
| Total | 100.0 |

Production Example 9

An O/W sunscreen which was an external preparation for skin of the present invention was prepared according to the recipe shown in Table 11. That is, the ingredients of A and B were heated at 80° C. respectively, and mixed together, then B was gradually added to A with stirring, and the mixture was cooled with stirring to yield an O/W sunscreen.

It was confirmed that this O/W sunscreen gave a skin whitening effect when applied to the skin.

TABLE 11

O/W sunscreen

| | | (% by mass) |
|---|---|---|
| A | Poly (ethylene glycol) | 0.5 |
| | 1,3-Butylene glycol | 5.0 |
| | Glycerol | 1.0 |
| | Pentylene glycol | 1.0 |
| | Ethanol | 1.0 |
| | Diglycerol | 0.5 |
| | Citric acid | 0.1 |
| | Sodium citrate | 0.1 |
| | Potassium hydroxide | 0.4 |
| | Triethanolamine | 0.4 |
| | Methylparaben | 0.2 |
| | Phenoxyethanol | 0.2 |
| | Pentasodium pentetate | 0.05 |
| | Phenylbenzimidazole sulfonic acid | 0.2 |
| | Ascorbic acid glucoside | 2.0 |

TABLE 11-continued

O/W sunscreen

| | | (% by mass) |
|---|---|---|
| | Xanthan gum | 0.1 |
| | Hydrochloride salt of Compound 1 | 1.0 |
| | Water | Balance |
| B | Mineral oil | 1.0 |
| | Petrolatum | 0.5 |
| | Microcrystalline wax | 0.5 |
| | Cetyl ethylhexanoate | 1.0 |
| | Glyceryl trioctanoate | 4.0 |
| | Beeswax | 0.5 |
| | Dimethicone | 0.5 |
| | Methylphenylpolysiloxane | 0.5 |
| | Decamethylcyclopentasiloxane | 3.0 |
| | Crosslinked dimethicone | 0.5 |
| | (Alkyl acrylate/dimethicone) copolymer | 0.5 |
| | t-Butyl methoxydibenzoylmethane | 1.0 |
| | Ethylhexyl methoxycinnamate | 3.0 |
| | Glyceryl oleate | 0.5 |
| | Polyglyceryl oleate | 0.5 |
| | Sorbitan isostearate | 0.5 |
| | PEG-20 stearate | 0.5 |
| | Sucrose stearate | 0.5 |
| | Polyoxyethylene phytostanol | 0.5 |
| | Polyoxyethylene polyglycerol stearyl ether | 0.3 |
| | Na Cocomonoglyceride sulfate | 0.1 |
| | Na Stearoyl lactylate | 0.1 |
| | PEG-10 dimethicone | 0.5 |
| | Stearic acid | 0.5 |
| | Cetanol | 1.0 |
| | Behenyl alcohol | 0.5 |
| | (Alkyl acrylate/dimethicone) copolymer-treated and oxidized titanium | 1.0 |
| | (Alkyl acrylate/dimethicone) copolymer-treated and oxidized Bengal red | 0.5 |
| | (Alkyl acrylate/dimethicone) copolymer-treated and oxidized yellow iron oxide | 0.1 |
| | (Alkyl acrylate/dimethicone) copolymer-treated and oxidizedb lack iron oxide | 0.01 |
| | Red No. 226 | 0.01 |
| | Triethoxycaprylylsilane-treated Yellow No. 4 | 0.01 |
| | Safflower red | 0.01 |
| | Gardenia yellow | 0.01 |
| | Gem Tone Ruby (produced by Engelhard Corp.) | 0.1 |
| | Timiron Splendid Gold (produced by Merck & Co., Inc.) | 0.1 |
| | Reflecks Pinpoints of Pearl (produced by Engelhard Corp.) | 0.1 |
| | Trimethoxysilyl dimethicone-treated COLORONA GLITTER Bordeaux (produced by Merck & Co., Inc.) | 0.1 |
| | Trimethoxysilyl dimethicone-treated GENESTAR 420 (produced by Nihon Koken Kogyo Co., Ltd.) | 0.1 |
| | Trimethoxysilyl dimethicone-treated COVERLEAF MF (produced by JGC Catalysts and Chemicals Ltd.) | 0.1 |
| | Perfluorooctyltriethoxysilane-treated COVERLEAF PC1035 (produced by JGC Catalysts and Chemicals Ltd.) | 0.1 |
| | SILKYFLAKE FTD025FY-F02 (produced by Nippon Sheet Glass Co., Ltd.) | 0.1 |
| | METASHINE MT1080KY (produced by Nippon Sheet Glass Co., Ltd.) | 0.1 |
| | Talc | 1.0 |
| | Methyl methacrylate crosspolymer | 1.0 |
| | Fine particle titanium oxide ("MT-100SA", produced by Tayca Corporation) | 6.0 |
| | Polyacrylate | 0.1 |
| | Fine particle zinc oxide | 2.0 |
| | Ethylhexylglycerin | 0.1 |
| | Tocopherol | 0.05 |
| | Perfume | 0.2 |
| | Total | 100.0 |

Production Example 10

A W/O sunscreen which was an external preparation for skin of the present invention was prepared according to the recipe shown in Table 12. That is, the ingredients of A and B were heated at 80° C. respectively, and mixed together, then A was gradually added to B with stirring, and the mixture was cooled with stirring to yield a W/O sunscreen.

It was confirmed that this W/O sunscreen gave a skin whitening effect when applied to the skin.

TABLE 12

W/O sunscreen

| | | (% by mass) |
|---|---|---|
| A | Poly(ethylene glycol) | 0.5 |
| | 1,3-Butylene glycol | 5.0 |
| | Glycerol | 1.0 |
| | Pentylene glycol | 2.0 |
| | Ethanol | 1.0 |
| | Diglycerol | 0.5 |
| | Citric acid | 0.1 |
| | Sodium citrate | 0.1 |
| | Potassium hydroxide | 0.4 |
| | Methylparaben | 0.2 |
| | Phenoxyethanol | 0.2 |
| | Pentasodium pentetate | 0.1 |
| | Phenylbenzimidazole sulfonic acid | 0.5 |
| | Ascorbic acid glucoside | 2.0 |
| | Xanthan gum | 0.1 |
| | Hydrochloride salt of Compound 1 | 1.0 |
| | Water | Balance |
| B | Mineral oil | 1.0 |
| | Petrolatum | 0.5 |
| | Microcrystalline wax | 0.5 |
| | Cetyl ethylhexanoate | 1.0 |
| | Glyceryl trioctanoate | 1.0 |
| | Beeswax | 0.5 |
| | Dimethicone | 0.5 |
| | Methylphenylpolysiloxane | 1.0 |
| | Decamethylcyclopentasiloxane | 14.0 |
| | Crosslinked dimethicone | 0.5 |
| | (Alkyl acrylate/dimethicone) copolymer | 0.5 |
| | Trimethylsiloxysilicate | 0.5 |
| | Caprylyl methicone | 0.5 |
| | t-Butyl methoxybenzoylmethane | 1.0 |
| | Ethylhexyl methoxycinnamate | 1.0 |
| | Glyceryl oleate | 0.5 |
| | Polyglyceryl oleate | 0.5 |
| | Sorbitan isostearate | 0.5 |
| | Sucrose stearate | 1.0 |
| | Polyoxyethylene polyglycerol stearyl ether | 0.5 |
| | PEG-10 dimethicone | 3.0 |
| | Dimethyl distearyl ammonium hectorite | 0.75 |
| | (Alkyl acrylate/dimethicone) copolymer-treated and oxidized titanium | 8.0 |
| | (Alkyl acrylate/dimethicone) copolymer-treated and oxidized Bengal red | 0.5 |
| | (Alkyl acrylate/dimethicone) copolymer-treated and oxidized yellow iron oxide | 1.5 |
| | (Alkyl acrylate/dimethicone) copolymer-treated and oxidized black iron oxide | 0.1 |
| | Red No. 226 | 0.01 |
| | Triethoxycaprylylsilane-treated Yellow No. 4 | 0.01 |
| | Safflower red | 0.01 |
| | Gardenia yellow | 0.01 |
| | Gem Tone Ruby (produced by Engelhard Corp.) | 0.2 |
| | Timiron Splendid Gold (produced by Merck & Co., Inc.) | 0.2 |
| | Reflecks Pinpoints of Pearl (produced by Engelhard Corp.) | 0.2 |
| | Trimethoxysilyl dimethicone-treated COLORONA GLITTER Bordeaux (produced by Merck & Co., Inc.) | 0.2 |
| | Trimethoxysilyl dimethicone-treated GENESTAR 420 (produced by Nihon Koken Kogyo Co., Ltd.) | 0.2 |
| | Trimethoxysilyl dimethicone-treated COVERLEAF MF (produced by JGC Catalysts and Chemicals Ltd.) | 0.2 |
| | Perfluorohexylethyl trimethoxysilane-treated COVERLEAF PC1035 (produced by JGC Catalysts and Chemicals Ltd.) | 0.2 |
| | SILKYFLAKE FTD025FY-F02 (produced by Nippon Sheet Glass Co., Ltd.) | 0.2 |

TABLE 12-continued

| W/O sunscreen | |
|---|---|
| | (% by mass) |
| METASHINE MT1080KY (produced by Nippon Sheet Glass Co., Ltd.) | 0.2 |
| Talc | 3.0 |
| Fine particle titanium oxide ("MT-100SA", produced by Tayca Corporation) | 1.0 |
| Fine particle zinc oxide | 0.5 |
| Ethylhexylglycerin | 0.2 |
| Tocopherol | 0.1 |
| Perfume | 0.2 |
| Total | 100.0 |

INDUSTRIAL APPLICABILITY

The skin whitening agent of the present invention exhibits an excellent skin whitening effect, and therefore it is extremely useful industrially, such that it can be suitably contained in a skin external composition for skin whitening.

What is claimed is:

1. A method of skin whitening comprising:
applying an agent comprising a compound expressed by the following Formula (1), or an acid addition salt thereof:

[Chem. 1]

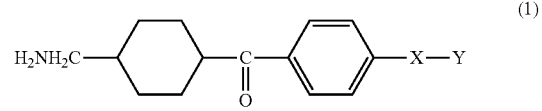

(1)

(wherein, X represents an alkylene group having 1 to 2 carbon atoms, where a hydrogen atom may be substituted with a methyl group; Y represents $COOR^1$ or $CH_2OR^2$; $R^1$ represents a hydrogen atom, or an optionally branched alkyl group having 1 to 6 carbon atoms; and $R^2$ represents a hydrogen atom or an optionally branched acyl group having 1 to 6 carbon atoms).

2. The method according to claim 1, wherein the agent is contained in a skin external composition.

3. The method according to claim 2, wherein the skin external composition is a cosmetic.

* * * * *